United States Patent
Maggio et al.

(10) Patent No.: US 8,476,389 B2
(45) Date of Patent: Jul. 2, 2013

(54) SILICONE HYDROGEL, LENS FOR EYE AND CONTACT LENS

(75) Inventors: Thomas L. Maggio, Jacksonville, FL (US); Michelle Carman Turnage, Jacksonville, FL (US); Kazuhiko Fujisawa, Shiga (JP); Masataka Nakamura, Shiga (JP)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 79 days.

(21) Appl. No.: 13/048,252

(22) Filed: Mar. 15, 2011

(65) Prior Publication Data

US 2011/0230589 A1    Sep. 22, 2011

(51) Int. Cl.
*C08F 30/08* (2006.01)

(52) U.S. Cl.
USPC .......................................................... 526/279

(58) Field of Classification Search
USPC .......................................................... 526/279
See application file for complete search history.

(56) References Cited

U.S. PATENT DOCUMENTS

| | | | |
|---|---|---|---|
| 4,711,943 A | 12/1987 | Harvey, III | |
| 4,834,753 A * | 5/1989 | Sulc et al. | 623/6.58 |
| 4,890,911 A * | 1/1990 | Sulc et al. | 351/159.33 |
| 5,336,797 A | 8/1994 | McGee et al. | |
| 5,399,737 A | 3/1995 | Park et al. | |
| 5,505,884 A | 4/1996 | Burke et al. | |
| 5,512,205 A | 4/1996 | Lai | |
| 5,994,488 A | 11/1999 | Yokota et al. | |
| 5,998,498 A | 12/1999 | Vanderlaan | |
| 6,020,445 A * | 2/2000 | Vanderlaan et al. | 526/279 |
| 6,367,929 B1 | 4/2002 | Maiden et al. | |
| 7,214,809 B2 * | 5/2007 | Zanini et al. | 556/419 |
| 7,396,890 B2 * | 7/2008 | Zanini et al. | 526/279 |
| 2004/0192872 A1 | 9/2004 | Iwata | |
| 2005/0176911 A1 * | 8/2005 | Zanini et al. | 528/32 |
| 2006/0072069 A1 | 4/2006 | Laredo et al. | |
| 2006/0165934 A1 * | 7/2006 | Okazaki et al. | 428/40.1 |
| 2006/0276608 A1 | 12/2006 | Lang | |
| 2007/0167592 A1 | 7/2007 | Zanini | |
| 2008/0045612 A1 | 2/2008 | Rathore et al. | |
| 2008/0121798 A1 | 5/2008 | Hieke | |
| 2008/0234457 A1 | 9/2008 | Zhou | |
| 2008/0305292 A1 * | 12/2008 | Okazaki et al. | 428/41.3 |
| 2010/0258961 A1 | 10/2010 | Chang | |
| 2011/0133350 A1 | 6/2011 | Qiu | |
| 2011/0211158 A1 | 9/2011 | Iwata | |

FOREIGN PATENT DOCUMENTS

| | | |
|---|---|---|
| EP | 1956033 B1 | 5/2009 |
| JP | 10212355 A | 8/1998 |
| WO | WO 2005078482 A1 | 8/2005 |
| WO | WO 2008005229 A2 | 1/2008 |
| WO | WO 2008005229 A3 | 1/2008 |
| WO | WO 2011005937 A2 | 1/2011 |
| WO | WO 2011005937 A3 | 1/2011 |

OTHER PUBLICATIONS

PCT International Search Report, dated Jun. 27, 2011, for PCT Int'l. Appln. No. PCT/2011/028842.
Andre Laschewsky et al., Macromol. Chem. Phys. 2001, vol. 202, pp. 276-286.
Volume III, Photoinitiators for Free Radical Cationic & Anionic Photopolymerization, 2nd Edition by J.V. Crivello & K. Dietliker; edited by G. Bradley; John Wiley and Sons; New York; 1998.
PCT International Search Report dated Oct. 13, 2011, for PCT Int'l. appln. No. PCT/US2011/028847.

* cited by examiner

*Primary Examiner* — James J Seidleck
*Assistant Examiner* — Peter A Salamon
(74) *Attorney, Agent, or Firm* — Karen A. Harding

(57) ABSTRACT

The present invention provides transparent silicone hydrogels with high acrylamide monomer content and an excellent balance between moisture content.
The silicone hydrogels may be obtained by polymerizing a monomer mix containing a plurality of monomers, wherein the monomer mix comprises about 30 to about 98% by weight of at least one type of silicone monomer which is, and about 1 to about 50% by weight of at least one type of non-silicone type (meth)acrylamide monomer containing two or more hydroxyl groups within a molecule; wherein the weight percents are based upon the total amount of monomer components and polymer components in the monomer mix.

19 Claims, No Drawings

SILICONE HYDROGEL, LENS FOR EYE AND CONTACT LENS

RELATED APPLICATIONS

This application claims priority to Japanese Patent Application No. JP2010-061991, filed Mar. 18, 2010.

BACKGROUND OF THE INVENTION

The present invention relates to a silicone hydrogel. This silicone hydrogel is suitable for use in medical implements such as ophthalmic lenses, endoscopes, catheters, transfusion tubes, gas transport tubes, stents, sheaths, cuffs, tube connectors, access ports, drainage bags, blood circuits, wound covering material, and various types of medicine carriers, but is particularly suitable for contact lenses, ophthalmic lenses, and artificial corneas.

DESCRIPTION OF THE RELATED ART

In recent years, silicone hydrogels have become known as materials for contact lenses that are used for extended wear. Silicone hydrogels are obtained by combining at least one silicone component and at least one hydrophilic component. For example, U.S. Pat. No. 7,396,890 and U.S. Pat. No. 7,214,809 disclose silicone hydrogels obtained by polymerizing a polymerization mix containing silicone (meth)acrylamide monomer and hydrophilic components, which may include a hydrophilic acrylamide monomer such as N,N-dimethylacrylamide, hydrophilic methacrylate ester such as 2-hydroxyethyl methacrylate, and an internal wetting agent.

However, the compositions can have relatively high amounts of methacrylate ester. While the acrylamide monomer has a higher polymerization rate constant than the methacrylate ester during homopolymerization, the rate of acrylamide and methacrylate copolymerization is significantly lower and as a result the polymerization rate of the entire system will be reduced.

On the other hand, U.S. Pat. No. 4,711,943 and Japanese Unexamined Patent Application H10-212355 disclose a silicone hydrogel containing a silicone acrylamide monomer and a hydrophilic acrylamide monomer. Acrylamide monomers account for the majority of these compositions, and a higher polymerization rate for the entire system is anticipated. However, the amido bond of the acrylamide group has high hydrophilicity, and therefore there are problems in that providing a transparent lens is difficult from the perspective of achieving both a sufficient amount of silicone component to provide desirable oxygen permeability and providing sufficient moisture content to provide flexibility to the lens. In particular, achieving a transparent lens is especially difficult if an internal wetting agent is added in order to increase the wettability of the surface.

On the other hand, Andre Laschewsky et al., Macromol. Chem. Phys. 2001, 202, 276 286 discloses a polymer that uses a hydrophilic acrylamide monomer with two or more hydroxyl groups in one molecule. However, neither copolymerization with a silicone monomer nor transparency and other physical properties of a copolymer are disclosed.

SUMMARY OF THE INVENTION

The present invention relates to silicone hydrogels with high acrylamide monomer content and an excellent balance between moisture content, modulus, wettability and transparency. This silicone hydrogel is suitably used for various types of medical devices, particularly for ophthalmic lenses such as contact lenses, intraocular lenses, and artificial cornea, and especially for contact lenses.

In order to achieve the aforementioned object, the present invention has the following composition. Namely, (1) A silicone hydrogel obtained by polymerizing a polymerization mix containing a plurality of monomers containing about 30 to about 98 weight % of at least one silicone monomer; and about 1 to about 50 weight % of at least one non-silicone (meth)acrylamide monomer represented by

[FORMULA 1]

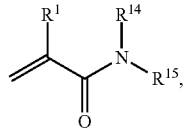

(c0)

wherein $R^1$ is hydrogen or methyl;
at least one of $R^{14}$ and $R^{15}$ is substituted with at least one C1-C20 alkyl substituted with at least one hydroxyl group, and
with the proviso that when;
i) one of $R^{14}$ and $R^{15}$ is hydrogen
ii) the other of $R^{14}$ and $R^{15}$ is substituted with at least two hydroxyl groups,
wherein said weight percent based upon total amount of monomer components and polymer components in the monomer mix.

The present invention further relates to medical devices made from the above described silicone hydrogels, including contact lenses, artificial corneas, endoscopes, catheters, transfusion tubes, gas transport tubes, stents, sheaths, cuffs, tube connectors, access ports, drainage bags, blood circuits, wound covering material, and medicine carriers.

The present invention further relates to a silicone hydrogel with high acrylamide monomer content and an excellent balance between moisture content, modulus, wettability and transparency. This silicone hydrogel is suitably used for various types of medical implements, particularly for ophthalmic lenses such as contact lenses, intraocular lenses, and artificial cornea, and especially for contact lenses.

DETAILED DESCRIPTION

As used herein the term (meth) or (methyl) designates optional methyl substitution. Thus, a term such as "(meth) acrylate" denotes both methacrylic and acrylic radicals.

The silicone hydrogel of the present invention is obtained by polymerizing a monomer mix comprising (A) from 30 to 98 weight % of at least one silicone monomer with regards to a total amount of monomer component and polymer component.

(B) from 1 to 50 weight % of a non-silicone (meth)acrylamide monomer having two or more hydroxyl groups in a molecule with regards to the total amount of monomer component and polymer component.

For the present invention, silicone monomer refers to a monomer comprising a polymerizable group and a siloxanyl group. A siloxanyl group refers to a group with at least one Si—O—Si bond.

Examples of silicone monomers that are used in the silicone hydrogel of the present invention are the silicone monomers expressed in the following general formulae (a1) through (a4).

[FORMULA 6]

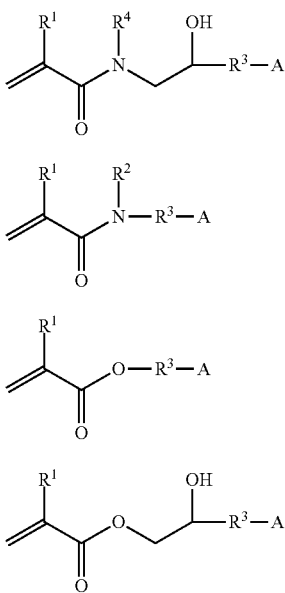

In formulae (a1) through (a4), $R^1$ independently represents a hydrogen atom or a methyl group. Of these, hydrogen atoms are preferable in order to further increase the polymerization rate.

$R^2$ represents an alkyl group with between 1 and 20 carbon atoms, in some embodiments between 1 and 10 carbon atoms, and in other embodiments between 1 and 6 carbon atoms, any of which are substituted with at least one hydroxyl group.

Examples include 2-hydroxyethyl groups, 2-hydroxypropyl groups, 3-hydroxypropyl groups, 2,3-dihydroxypropyl groups, 4-hydroxy butyl groups, 2-hydroxy-1,1-bis(hydroxymethyl)ethyl groups, 2-hydroxymethylphenyl groups, 3-hydroxymethylphenyl groups, 4-hydroxymethylphenyl groups and the like. In one embodiment $R^2$ is selected from 2-hydroxyethyl groups, 2-hydroxypropyl groups and 2,3-dihydroxypropyl groups, and in another embodiment $R^2$ is a 2,3-dihydroxypropyl group.

$R^3$ represents an alkylene group having between 1 and 20 carbon atoms or an arylene group having between 6 and 20 carbon atoms, which may be unsubstituted or can independently have substitution groups such as with hydroxyl, acid, ester, ether, thiol and combinations thereof. In one embodiment $R^3$ represents a C1-10 alkylene which may be unsubstituted or independently substituted with hydroxyl, acid, ester, ether, thiol and combinations thereof. Examples thereof include methylene groups, ethylene groups, propylene groups, butylene groups, pentalene groups, octalene groups, decylene groups, and phenylene groups and the like. These alkylene and arylene groups can be straight or branched. In another embodiment $R^2$ is selected from $C_{1-5}$ alkylene groups, which may be unsubstituted or substituted with hydroxyl, ether groups and combinations thereof. In another embodiment $R^2$ is selected from C2-5 alkylene groups, which may be unsubstituted or substituted with hydroxyl, ether groups and combinations thereof, and in yet another embodiment, $R^2$ is a $C_3$ alkylene groups, which may be unsubstituted or substituted with hydroxyl, ether groups and combinations thereof.

$R^4$ represents a hydrogen atom or an alkyl or aryl group with between 1 and 20 carbon atoms which may be substituted with hydroxyl, acid, ester, ether, thiol and combinations thereof. Examples thereof include hydrogen atoms, methyl groups, ethyl groups, propyl groups, n-propyl groups, i-propyl groups, n-butyl groups, s-butyl groups, t-butyl groups, n-pentyl groups, i-pentyl groups, s-pentyl groups, neopentyl groups, hexyl groups, heptyl groups, octyl groups, nonyl groups, decyl groups, dodecyl groups, eicosyl groups, phenyl groups, naphthyl groups, and the like. These alkyl groups can be straight or branched. If the number of carbon atoms in $R^4$ is too high, the silicone content will be relatively low, and therefore a hydrogen atom or an alkyl or aryl group with between 1 and 10 carbon atoms is more preferable, and a hydrogen atom or an alkyl group with between 1 and 4 for carbon atoms is most preferable.

A represents a siloxanyl group. Preferable examples thereof include the silicone groups expressed by the following general formula (f):

[FORMULA 7]

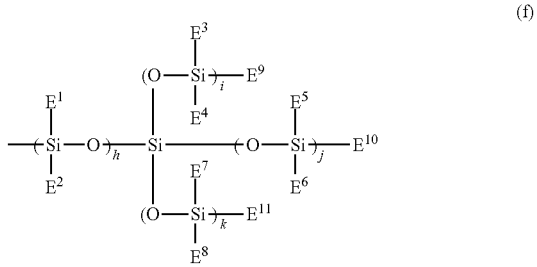

In general formula (f), $E^1$ through $E^{11}$ independently represent a hydrogen atom, an alkyl group with between 1 and 20 carbon atoms, in some embodiments between 1 and 10 carbon atoms and in other embodiments between 1 and 6 carbon atoms, any of which may be substituted with fluorine, hydroxyl, acid, ester, ether, thiol and combinations thereof, or an aryl group with between 6 and 20 carbon atoms which may be substituted with fluorine, hydroxyl, acid, ester, ether, thiol and combinations thereof.

In general formula (f), h represents an integer from 0 to 200, and i, j, and k independently represent integers from 0 to 20 (excluding the case where h=i=j=k=0). If the total of h+i+j+k is too small, sufficient oxygen permeability will not be achieved, but if too large, the compatibility with the hydrophilic monomer will decrease. Therefore a total between 2 and 100 is preferable, between 2 and 10 is more preferable, and between 3 and 10 is most preferable. Furthermore, i=j=k=0 is preferable from the perspective of the shape recovery of the polymer obtained by polymerizing the silicone prepolymer obtained.

Of the foregoing, the silicone (meth)acrylamide monomer expressed by general formulae (a1) and (a2) are preferable from a perspective of increasing the polymerization rate of the entire system.

More specific examples of the structure of the silicone (meth)acrylamide monomers expressed by general formulae (a1) and (a2) are the silicone (meth)acrylamide monomers expressed by general formulae (b1) through (b4).

[FORMULA 8]

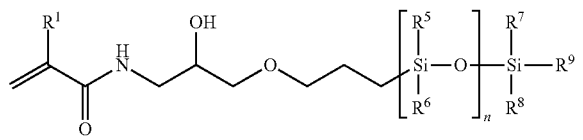
(b1)

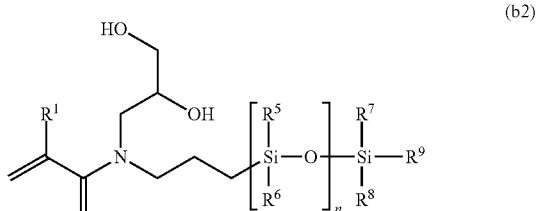
(b2)

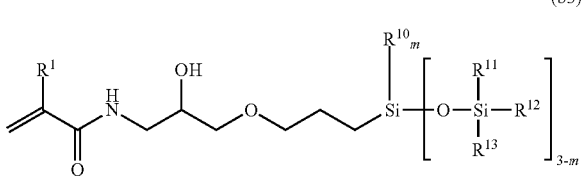
(b3)

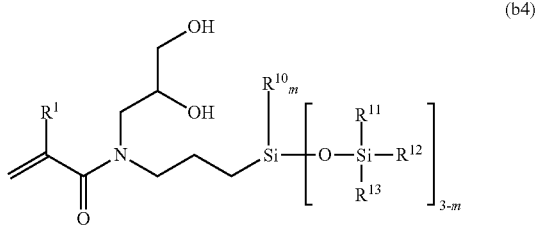
(b4)

In the chemical formulae (b1) to (b4), $R^1$ independently represents a hydrogen atom or a methyl group. Of these, hydrogen atoms are more preferable from the perspective of increasing the polymerization rate.

$R^5$ to $R^{13}$ independently represent alkyl groups having between 1 and 20 carbon atoms or aryl groups having between 6 and 20 carbon atoms. If the number of carbon atoms of $R^5$ through $R^8$ is too high, a silicon atom content will be relatively low, leading to a reduction in the oxygen permeability of the silicone hydrogel. Therefore an alkyl group with between 1 and 10 carbon atoms or an aryl group with between 6 and 10 carbon atoms is more preferable, and alkyl group with between 1 and 4 carbon atoms is even more preferable, and a methyl group which has 1 carbon atom is most preferable. If the number of carbon atoms in $R^9$ is too low, the polysiloxane chain will easily hydrolyze, but if too high, the silicone hydrogel will tend to have lower oxygen permeability. Therefore, an alkyl group with between 1 and 10 carbon atoms or an aryl group with between 6 and 10 carbon atoms is more preferable, an alkyl group with between 1 and 6 carbon atoms is even more preferable, and an alkyl group with between 1 and 4 carbon atoms is most preferable. If the number of carbon atoms in $R^9$ through $R^{13}$ is too high, the oxygen permeability of the silicone hydrogel will be too low, and therefore an alkyl group between 1 and 10 carbon atoms or an aryl group with between 6 and 10 carbon atoms is more preferable, an alkyl group with between 1 and 4 carbon atoms is even more preferable, and a methyl group or ethyl group is most preferable.

n is a natural number in the range from 1 to 50. If n is too small, sufficient oxygen permeability will not be achieved, but if too large, a compatibility with the hydrophilic monomer will decrease. Therefore a value between 2 and 30 is preferable, between 3 and 10 is more preferable, and between 3 and 10 is most preferable.

m represents a natural number from 0 to 2. m is more preferably 0 or 1 in order to obtain sufficient oxygen permeability.

Of the silicone (meth)acrylamide monomers expressed by general formulae (b1) through (b4) the silicone (meth)acrylamide monomers expressed by general formulae (b1) and (b2) are preferable from a perspective that a form recovery of the silicone hydrogel obtained will be favorable because the siloxanyl group is a straight chain, and the silicone (meth) acrylamide monomers expressed by general formula (b2) are most preferable from a perspective of the transparency of the silicone hydrogel obtained.

If the amount of silicone monomer used in the silicone hydrogel of the present invention is too low, the oxygen permeability of the silicone hydrogel will be insufficient, but if the amount is too high, the hydrophilicity will be insufficient, so the monomer and polymer components in the monomer mix must be between 30 and 98 weight %, preferably between 40 and 80 weight %, and more preferably between 50 and 70 weight %. A lower limit value is preferably 30 weight %, more preferably 40 weight %, and even more preferably 50 weight %. An upper limit value is preferably 98 weight %, more preferably 80 weight %, and even more preferably 70 weight %. Any of the preferred lower limit values and any of the preferred upper limit values can be combined together. In the silicone hydrogel of the present invention, the monomer and polymer component in the monomer mix contains between 1 and 50 weight % of a non-silicone (meth)acrylamide monomer expressed by the following formula (c0)

[FORMULA 9]

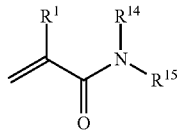
(c0)

In chemical formula (c0), $R^1$ is hydrogen or methyl. At least one of $R^{14}$ and $R^{15}$ is substituted with at least C1-C20 alkyl substituted with at least one hydroxyl group, and with the proviso that when i) one of $R^{14}$ and $R^{15}$ is hydrogen, ii) the other of $R^{14}$ and $R^{15}$ is a C1-C20 alkyl group substituted with two or more hydroxyl groups substituted with one hydroxyl group, weight percent reported in the present application are based upon total amount of monomer components and polymer components in the monomer mix. Incidentally, with the present invention, the non-silicone (meth)acrylamide monomer refers to (meth)acrylamide monomers that do not contain a siloxanyl group in the molecule.

In one embodiment, the non-silicone (meth)acrylamide monomer comprises two or more hydroxyl groups in the molecule. In chemical formula (c0) of this embodiment, $R^1$ represents hydrogen or methyl group. In some embodiments hydrogen atoms are more preferable from the perspective of increasing the polymerization rate. In this embodiment at least one of $R^{14}$ and $R^{15}$ is selected from hydrogen, optionally substituted C1-C20 alkyl group, or optionally substituted C6-C20 aryl group with the proviso that the total number of hydroxyl groups in $R^{14}$ and $R^{15}$ is two or more. In one embodiment $R^{14}$ and $R^{15}$ is are independently selected from C1-C10 alkyl group which may be substituted with at least one more hydroxyl group, and in other embodiments C1-C6 alkyl group which may be substituted with at least one more hydroxyl group, so long as the non-silicone (meth)acrylamide meets the proviso above. Examples of $R^{14}$ and $R^{15}$ include hydrogen atoms, methyl groups, ethyl groups, propyl groups, n-propyl groups, i-propyl groups, n-butyl groups, s-butyl groups, t-butyl groups, n-pentyl groups, i-pentyl groups, s-pentyl groups, neopentyl groups, hexyl groups, heptyl groups, octyl groups, nonyl groups, decyl groups, dodecyl groups, eicosyl groups, phenyl groups, naphthyl groups, 2-hydroxyethyl groups, 2-hydroxypropyl groups, 3-hydroxypropyl groups, 2,3-dihydroxypropyl groups, 4-hydroxy butyl groups, 2-hydroxy-1,1-bis(hydroxymethyl)ethyl groups, 2-hydroxymethylphenyl groups, 3-hydroxymethylphenyl groups, 4-hydroxymethylphenyl groups and the like. These alkyl and hydroxyalkyl groups can be straight or branched. A particularly preferable example of a non-silicone type (meth)acrylamide monomer containing two or more hydroxyl groups in the molecule include the monomers expressed by the following general formulae (c1) through (c3).

[FORMULA 10]

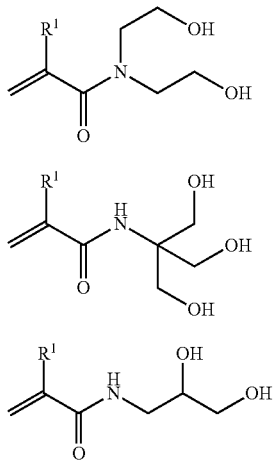

(c1)

(c2)

(c3)

In chemical formulae (c1) through (c3), $R^1$ independently represents a hydrogen atom or a methyl group. In some embodiments hydrogen atoms are more preferable from the perspective of increasing the polymerization rate. Furthermore, of these monomers, the monomers expressed by formula (c1) produced contact lenses having superior clarity when polymerized with the other components used in the present examples.

In another embodiment, a non-silicone (meth)acrylamide monomer comprises one hydroxyl group and no amide hydrogen in the molecule. In chemical formula (c0) of this embodiment, $R^1$ represents hydrogen or methyl group. In some embodiments hydrogen atoms are more preferable from the perspective of increasing the polymerization rate. Preferably $R^{14}$ and $R^{15}$ are independently selected from optionally substituted C1-C20 alkyl group, or optionally substituted C6-C20 aryl group with the proviso that one of $R^{14}$ and $R^{15}$ is substituted with at least one hydroxyl group.

Examples of $R^{14}$ and $R^{15}$ include methyl groups, ethyl groups, propyl groups, n-propyl groups, i-propyl groups, n-butyl groups, s-butyl groups, t-butyl groups, n-pentyl groups, i-pentyl groups, s-pentyl groups, neopentyl groups, hexyl groups, heptyl groups, octyl groups, nonyl groups, decyl groups, dodecyl groups, eicosyl groups, phenyl groups, naphthyl groups, 2-hydroxyethyl groups, 2-hydroxypropyl groups, 3-hydroxypropyl groups, 4-hydroxy butyl groups, 2-hydroxymethylphenyl groups, 3-hydroxymethylphenyl groups, 4-hydroxymethylphenyl groups and the like. These alkyl groups can be straight or branched. Examples of non-silicone (meth)acrylamide monomer with a hydroxyl group and no amide hydrogen in the molecule include the monomers expressed by the following general formulae (c11) through (c13).

[FORMULA 11]

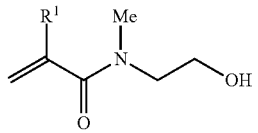

(c11)

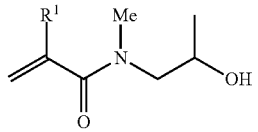

(c12)

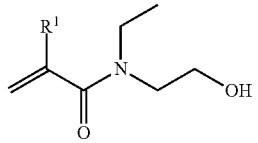

(c13)

In chemical formulae (c11) through (c13), $R^1$ independently represents a hydrogen atom or a methyl group. In some embodiments hydrogen atoms are more preferable from the perspective of increasing the polymerization rate. Furthermore, of these monomers, the monomers expressed by formula (c11) are most preferable from the perspective of the transparency of the silicone hydrogel obtained.

From the perspective of low modulus of the silicone hydrogel obtained, acrylamide monomer comprising one hydroxyl group and one amide hydrogen in the molecule is preferable. Examples of an acrylamide monomer comprising one hydroxyl group and one amide hydrogen in the molecule include N-(mono-hydroxyl substituted C1-C20 alkyl)acrylamide and N-(mono-hydroxyl substituted C6-C20 aryl)acrylamide. More specific examples include N-(2-hydroxyethyl)acrylamide, N-(2-hydroxypropyl)acrylamide, N-(3-hydroxypropyl)acrylamide, N-(2-hydroxybutyl)acrylamide, N-(3-hydroxybutyl)acrylamide, N-(4-hydroxy butyl)acrylamide, N-(2-hydroxymethylphenyl)acrylamide, N-(3-hydroxymethylphenyl)acrylamide, N-(4-hydroxymethylphenyl)acrylamide and the like. These alkyl and aryl groups can be straight or branched. From the perspective of low modulus of the silicone hydrogel obtained, N-(mono-hydroxyl substituted C2-C4 alkyl)acrylamide is more preferable, and N-(2-hydroxyethyl)acrylamide is most preferable.

If the amount of non-silicone (meth)acyrlamide monomer is too low, the silicone hydrogel will have low transparency or high modulus or both, but if the amount is too high, the silicone hydrogel will have low oxygen permeability, and therefore the amount is between 1 and 50 weight %, in some embodiments between 2 and 30 weight %, and in other embodiments between 3 and 20 weight %, and in others between about 5 and about 15 weight %, based on the monomer and polymer component in the monomer mix.

Suitable lower limit values include about 1 weight %, about 2 weight %, about 3 weight %, and about 5 weight %. Suitable upper limit values include about 50 weight %, about 30 weight %, about 20 weight %, and about 15 weight %. Any of the preferred lower limit values and any of the preferred upper limit values can be combined together. The monomer mix for obtaining silicone hydrogels of the present invention may also contain reactive and non-reactive wetting agents.

Suitable wetting agents include hydrophilic polymer with a molecular weight of about 1000 or more. The hydrophilic polymers may be incorporated into the monomer mix in amounts from about 1 to about 30% by weight with respect to the total amount of monomer components and polymer components.

Examples of hydrophilic polymers that may be used in the silicone hydrogel of the present invention include poly-N-vinyl pyrrolidone, poly-N-vinyl-2-piperidone, poly-N-vinyl-2-caprolactam, poly-N-vinyl-3-methyl-2-caprolactam, poly-N-vinyl-3-methyl-2-piperidone, poly-N-vinyl-4-methyl-2-piperidone, poly-N-vinyl-4-methyl-2-caprolactam, poly-N-vinyl-3-ethyl-2-pyrrolidone, poly-N-vinyl-4,5-dimethyl-2-pyrrolidone, polyvinyl imidazole, poly-N-vinyl formamide, poly-N-vinyl(methyl)acetamide, poly-N-methyl-N-vinyl (methyl)acetamide, poly-N-vinyl-N-(methyl)propionamide, poly-N-vinyl-N-methyl-2-(methyl)propionamide, poly-N-vinyl-2-(methyl)propionamide, poly-N-vinyl-N,N'-dimethylurea poly-N,N-dimethyl acrylamide, poly-N,N-diethyl acrylamide, poly-N-isopropyl acrylamide, polyvinyl alcohol, polyacrylate, polyethylene oxide, poly-2-ethyl oxazoline, heparine, polysaccharide, poly-acryloyl morpholine, and mixtures and copolymers thereof. The hydrophilic polymers selected from polyvinylpyrrolidone, poly-N,N-dimethyl acrylamide, polyacrylic acid, polyvinyl alcohol, poly-N-methyl-N-vinyl(methyl)acetamide and copolymers and mixtures thereof are may be particularly effective at enhancing the wettability of certain silicone hydrogels. Polyvinylpyrrolidone and poly-N,N-dimethyl acrylamide provide a balance between the wettability of the silicone hydrogel and the compatibility to the monomer mix in certain formulations. Examples of suitable wetting agents are disclosed in US2006-0072069A1, U.S. Pat. No. 6,367,929 and US-2008-0045612A1.

If the amount of hydrophilic polymer that is used in the silicone hydrogel of the present invention is too low, the desired wettability may not be achieved, but if too high, the hydrophilic polymer may not easily dissolve in the monomer mix, and therefore the amount is between about 1 and about 30 weight %, in some embodiments between about 2 and about 25 weight %, in other embodiments between about 3 and about 20 weight %, and other embodiments between about 6 and about 20 weight % of the monomer and polymer component in the monomer mix. Lower limit values include about 1 weight %, about 2 weight %, preferably about 3 weight %, and about 6 weight %. Upper limit values include about 30 weight %, about 25 weight %, about 20 weight %, about 9 weight %. Any of the lower limit values and any of the upper limit values can be combined together.

If the molecular weight of the hydrophilic polymer that is used in the silicone hydrogel of the present invention is too low, desirable wettability may not be provided, but if too high, the solubility in the monomer mix may be inferior, and viscosity of the monomer mix will be increased. In one embodiment the molecular weight is preferably between 1000 Daltons and 10 million Daltons, in some embodiments between 100,000 Daltons and 1 million Daltons, and in other embodiments between 200,000 and 800,000. In embodiments where the hydrophilic polymer comprises at least one reactive group capable of covalently bonding with the silicone hydrogel matrix, the molecular weight may be at least about 2000 Daltons, at least about 5,000 Daltons; and in some embodiments between about 5,000 to about 180,000 Daltons, or between about 5,000 to about 150,000 Daltons. Lower limit values include about 1000 Daltons, about 100,000 Daltons, and about 200,000 Daltons. Upper limit values include about 10 million Daltons, about 1 million Daltons, and about 800,000 Daltons. Any of the preferred lower limit values and any of the preferred upper limit values can be combined together. The molecular weight of the hydrophilic polymer of the present invention is expressed by the weighted average molecular weight (Mw) measured by gel permeation chromatography (column: TSK gel GMPWXL manufactured by Tosoh Corporation, mobility phase: water/methanol=50/50, 0.1 N lithium nitrate added, flow rate: 0.5 mL/minute, detector: differential refractive index detector, molecular weight standard sample: polyethylene glycol).

In one embodiment, the monomer mix for obtaining the silicone hydrogel of the present invention preferably also satisfies the following condition (D).

(D) At least a part of the silicone monomers is silicone (meth)acrylamide monomer, and the total amount of all (meth)acrylamide monomers (silicone and non-silicone (meth)acrylamide monomers) is about 90% or more by weight with respect to the total amount of monomer components in the monomer mix.

Of the monomer components used for polymerizing the silicon hydrogel of the present invention, if the amount of non-acrylamide monomer is too high, the overall polymerization rate will be decreased, so the total amount all of (meth)acrylamide monomers (silicone and non-silicone (meth)acrylamide monomers) is in one embodiment about 90 weight % or higher, in another about 95 weight % or higher.

The silicone hydrogel of the present invention can also contain a second non-silicone type amide monomer in addition to the non-silicone type acrylamide monomer containing two or more hydroxyl groups in the molecule. Examples thereof include (meth)acrylamide, N,N-dimethyl(meth)acrylamide, N,N-diethyl(meth)acrylamide, N-isopropyl(meth)acrylamide, (meth)acryloyl morpholine, N-methoxymethyl (meth)acrylamide, N-hydroxymethyl(meth)acrylamide, N-(2-hydroxyethyl)(meth)acrylamide, and the like. Of these, N,N-dimethylacrylamide is preferable from a perspective of a balance between hydrophilicity and compatibility with the silicone monomer, and the polymerization rate.

If the amount of the second non-silicone type (meth)acrylamide monomer that is used is too high, the oxygen permeability will be reduced, but if too low, the silicone hydrogels will be too hard, and therefore the amount of the second non-silicone type (meth)acrylamide monomer in this embodiment is between about 1 and about 50 weight %, more preferably between about 10 and about 40 weight %, and most preferably between 15 and 35 weight %, based on the monomer and polymer component in the monomer mix. Lower limit values are about 1 weight %, about 10 weight %, and about 15 weight %. Upper limit values are about 50 weight %, about 40 weight %, and about 35 weight %. Any of the lower limit values and any of the upper limit values can be combined together.

The silicone hydrogel of the present invention may also include a monomer with two or more polymeric groups as a copolymerization component. In this case, the silicone hydrogel of the present convention is made to be solvent resistant.

Preferable examples of monomers with two or more polymeric groups include bifunctional and polyfunctional acrylates such as ethylene glycol(meth)acrylate, diethylene glycol di(meth)acrylate, triethylene glycol di(meth)acrylate, neopentyl glycol di(meth)acrylate, tetraethylene glycol di(meth)acrylate, glyceryl tri(meth)acrylate, pentaerythritol tetra(meth)acrylate, and trimethylol propane tri(meth)acrylate, and bisacrylamides such as N,N'-methylene bisacrylamide, N,N'-ethylene bisacrylamide, N,N'-propylene bisacrylamide, and the like. Of these, the bisacrylamides are preferable from a perspective of increased polymerization rate, and of these, N,N'-methylene bisacrylamide and N,N'-ethylene bisacrylamide are preferable. The amount of monomer containing two or more polymeric groups that is used is between about 0.1 and about 10 weight %, in some embodiments between about 0.5 and about 8 weight %, and in other embodiments between about 0.8 and about 5 weight %. Lower limit values include about 0.1 weight %, about 0.5 weight %, and about 0.8 weight %. Upper limit values include about 10 weight %, about 8 weight %, and about 5 weight %. Any of the preferred lower limit values and any of the preferred upper limit values can be combined together.

When obtaining the silicone hydrogel of the present invention by polymerization, a polymerization initiator may also be added to enhance polymerization. Suitable initiators include thermal polymerization initiator such as a peroxide compound or an azo compound, or a photopolymerization initiators (which may be UV, visible or a combination), or mixtures thereof. If thermal polymerization is used, a thermal polymerization initiator that has optimal decomposition properties at the desired reaction temperature is selected and used. Generally, an azo type initiator or a peroxide type initiator where the 10 hour half-life temperature is between about 40° C. and about 120° C. is preferable. Examples of photopolymerization initiators include carbonyl compounds, peroxide compounds, azo compounds, sulfur compounds, halogenated compounds, metal salts, and the like. More specific examples of photoinitiators include as aromatic alpha-hydroxy ketones, alkoxyoxybenzoins, acetophenones, acylphosphine oxides, bisacylphosphine oxides, and a tertiary amine plus a diketone, mixtures thereof and the like. Illustrative examples of photoinitiators are 1-hydroxycyclohexyl phenyl ketone, 2-hydroxy-2-methyl-1-phenyl-propan-1-one, bis(2,6-dimethoxybenzoyl)-2,4-4-trimethylpentyl phosphine oxide (DMBAPO), bis(2,4,6-trimethylbenzoyl)-phenyl phosphineoxide (Irgacure 819), 2,4,6-trimethylbenzyldiphenyl phosphine oxide and 2,4,6-trimethylbenzoyl diphenylphosphine oxide, benzoin methyl ether and a combination of camphorquinone and ethyl 4-(N,N-dimethylamino)benzoate. Commercially available visible light initiator systems include Irgacure 819, Irgacure 1700, Irgacure 1800, Irgacure 819, Irgacure 1850 (all from BASF) and Lucirin TPO initiator (available from BASF). Commercially available UV photoinitiators include Darocur 1173 and Darocur 2959 (BASF). These and other photoinitiators which may be used are disclosed in Volume III, Photoinitiators for Free Radical Cationic & Anionic Photopolymerization, $2^{nd}$ Edition by J. V. Crivello & K. Dietliker; edited by G Bradley; John Wiley and Sons; New York; 1998, which is incorporated herein by reference. These polymerization initiators can be used independently or blended together, and the amount used is approximately 1 weight % for 100 weight % of monomer component.

Other components that can be present in the reaction mixture used to form the contact lenses of this invention include, ultra-violet absorbing compounds, medicinal compounds, nutriceutical compounds, antimicrobial compounds, copolymerizable and nonpolymerizable dyes, including dyes and compounds which reversibly change color or reflect light when exposed to various wavelengths of light, release agents, reactive tints, pigments, combinations thereof and the like.

When obtaining the silicone hydrogel of the present invention by polymerization, a polymerization solvent can be used. The solvent can be any type of organic or inorganic solvent. Examples that can be used include water, methanol, ethanol, propanol, 2-propanol, butanol, tert-butanol, tert-amyl alcohol, 3,7-dimethyl-3-octanol, tetrahydrolinalool, and other alcohol type solvents; benzene, toluene, xylene, and other types of aromatic hydrocarbon solvents; hexane, heptane, octane, decane, petroleum ether, kerosene, ligroin, paraffin, and other types of aliphatic hydrocarbon solvents; acetone, methyl ethyl ketone, methyl isobutyl ketone, and other ketone type solvents; ethyl acetate, butyl acetate, methyl benzoate, dioctyl phthalate, ethylene glycol diacetate, and other ester type solvents; diethyl ether, tetrahydrofuran, dioxane, ethylene glycol dialkyl ether, diethylene glycol dialkyl ether, triethylene glycol dialkyl ether, tetraethyleneglycol dialkyl ether, polyethylene glycol dialkyl ether, polyethylene glycol-poly propylene glycol block copolymer, polyethylene glycol-poly propylene glycol random copolymer, and other types of glycol ether solvents. The solvents can be used individually or combined. Of these, alcohol type solvents and glycol ether type solvents are preferable from a perspective that the solvents can easily be removed from the silicone hydrogel obtained by washing with water Solvents useful in preparing the devices of this invention include ethers, esters, alkanes, alkyl halides, silanes and alcohols. Examples of ethers useful as diluents for this invention include tetrahydrofuran. Examples of esters useful for this invention include ethyl acetate. Examples of alkyl halides useful as diluents for this invention include methylene chloride. Examples of silanes useful as diluents for this invention include octamethylcyclotetrasiloxane. Examples of alcohols useful as diluents for this invention include hexanol, heptanol, octanol, nonanol, decanol, tert-butyl alcohol, 3-methyl-3-pentanol, isopropanol, and 3,7-dimethyl-3-octanol. Additional diluents useful for this invention are disclosed in U.S. Pat. No. 6,020,445, which is incorporated herein by reference.

The silicone hydrogel of the present invention can be used independently by molding into the desired shape, but can also be blended with other materials and then molded. Furthermore, a coating may be applied to the surface of the molded parts.

Applications for the silicone hydrogels of the present invention include ophthalmic lenses, endoscopes, catheters, transfusion tubes, gas transport tubes, stents, sheaths, cuffs, tube connectors, access ports, drainage bags, blood circuits, wound covering material, and various types of medicine carriers, but contact lenses, intraocular lenses, artificial cornea, cornea inlays, and cornea onlays are particularly suitable, and contact lenses are most suitable.

When the silicone hydrogel of the present invention is molded and used as an ophthalmic lens, the polymerization method and molding method can be standard methods as follows. Examples include a method of first molding the silicone hydrogel into a round bar or plate and then machining to the desired shape by a cutting or lathing process or the like, a mold polymerization method, a spin cast method, and the like.

As one example, the case where an ophthalmic lens is made from the silicone hydrogel of the present invention using a mold polymerization method is described next.

A monomer composition is injected into the space between two molds which have a lens shape. Next, photopolymerization or thermal polymerization is performed to form the lens shape. The mold is made from plastic, glass, ceramic, metal, or the like, but for the case of photo polymerization, an material which is transparent to the photopolymerization wavelength is used, and normally plastic or glass is used. When manufacturing the silicone hydrogel, a space is formed by two counterfacing molds, and the monomer composition is injected into the space. Next, the mold with the space filled with the monomer composition is irradiated with an activating light such as ultraviolet light, visible light or a combination thereof, or placed in an oven or bath and heated to polymerize the monomer. It is also possible to use both methods, by thermal polymerization after photopolymerization or conversely by using photopolymerization after thermal polymerization. For the case of photopolymerization, generally a light containing a high level of light from a light source, such as a mercury lamp or a fluorescent lamp for example, is irradiated for a short period of time (normally 1 hour or less). When performing thermal polymerization, conditions where the temperature is gradually increased from near room temperature to a high temperature of between about 60° C. and about 200° C. over the course of several hours to several tens of hours is preferable in order to maintain the optical consistency and quality of the polymer and to increase the reproducibility.

The silicone hydrogel of the present invention can be modified by various methods. If the application is an ophthalmic lens, and a hydrophilic polymer is not internally included, a modification process may be performed in order to improve the wetting properties of the lens.

Specific modification methods include electromagnetic (including light) irradiation, plasma irradiation, vapor deposition, chemical vapor deposition treatment such as sputtering, heating, mold transfer coating, charge association coatings, base treatments, acid treatments, and treatments with other suitable surface treatment agents, and combinations thereof can also be used.

Examples of a base treatment or acid treatment include a method of bringing a molded part into contact with a basic or acidic solution, or a method of bringing a molded part into contact with a basic or acidic gas. More specific methods include, for example, a method of immersing a molded parts in a basic or acidic solution, a method of spraying a basic or acidic solution or a basic or acidic gas onto a molded parts, a method of applying a basic or acidic solution onto a molded part using a paddle or brush or the like, a method of spin coating a basic or acidic solution onto a molded part, a dip coat method, and the like. The simplest method that provides a large modification affect is a method of immersing a molded part in a basic or acidic solution.

The temperature when immersing the silicon hydrogel in a basic or acidic solution is not particularly restricted, but normally the temperature is within a range between approximately about −50° C. and about 300° C. When considering an ease of work, a temperature range between about −10° C. and about 150° C. is more preferable, and a range between about −5° C. and about 60° C. is most preferable.

The optimum time that the silicone hydrogel is immersed in the basic or acidic solution varies depending on the temperature, but generally 100 hours or less is preferable, 24 hours or less is more preferable, and 12 hours or less is most preferable. If the contact time is too long, not only will the ease of work and the productivity be inferior, but there may also be negative effects such as reducing the oxygen permeability and degrading the mechanical properties.

Examples of bases that can be used include alkali metal hydroxides, alkali earth metal hydroxides, various types of carbonates, various types of borates, various types of phosphates, ammonia, various ammonium salts, various amines, and polymer bases such as polyethyleneimine and polyvinyl amine and the like. Of these, alkali metal hydroxides are most preferable because of the low cost and the strong treatment effect. Examples of acids that can be used include various types of inorganic acids such as sulfuric acid, phosphoric acid, hydrochloric acid, and nitric acid; various types of organic acids such as acetic acid, formic acid, benzoic acid, and phenol; and various types of polymer acids such as polyacrylic acid and polystyrene sulfonic acid and the like. Of these, polymer acids are most preferable because the treatment effect is strong and the negative effect on other physical properties is minimal.

The solvent for the basic or acidic solution can be any type of inorganic or organic solvent. Examples include water, methanol, ethanol, propanol, 2-propanol, butanol, ethylene glycol, diethylene glycol, triethylene glycol, tetraethyleneglycol, polyethylene glycol, glycerin, and other alcohols, benzene, toluene, xylene, and other aromatic hydrocarbons, hexane, heptane, octane, decane, petroleum ether, kerosene, ligroin, paraffin, and other aliphatic hydrocarbons, acetone, methyl ethyl ketone, methyl isobutyl ketone, and other ketones, ethyl acetate, butyl acetate, methyl benzoate, dioctyl phthalate, and other esters, diethyl ether, tetrahydrofuran, dioxane, ethylene glycol dialkyl ether, diethyl glycol dialkyl ether, triethylene glycol dialkyl ether, tetraethyleneglycol dialkyl ether, polyethylene glycol dialkyl ether and other ethers; dimethylformamide, dimethyl acetoamide, N-methyl-2-pyrrolidone, dimethyl imidazolidinone, hexamethyl phospholic triamide, dimethyl sulfoxide and other non-protonic polar solvents, methylene chloride, chloroform, dichloroethane, trichloroethane, trichloroethylene, other halogen type solvents, and freon type solvents.

Of these, water is most preferable from the perspective of economics, simplicity of handling, and chemical stability and the like. The solvent can also be a blend of two or more types.

With the present invention, the basic or acidic solution that is used may contain components other than the basic or acidic substance and the solvent.

The basic or acidic substance can be removed from the silicone hydrogel by washing after the basic or acidic treatment.

The washing solvent can be any type of inorganic or organic solvent. Examples include water, methanol, ethanol, propanol, 2-propanol, butanol, ethylene glycol, diethylene glycol, triethylene glycol, tetraethyleneglycol, polyethylene glycol, glycerin, and other alcohols, benzene, toluene, xylene, and other aromatic hydrocarbons, hexane, heptane, octane, decane, petroleum ether, kerosene, ligroin, paraffin, and other aliphatic hydrocarbons, acetone, methyl ethyl ketone, methyl isobutyl ketone, and other ketones, ethyl acetate, butyl acetate, methyl benzoate, dioctyl phthalate, and other esters, diethyl ether, tetrahydrofuran, dioxane, ethylene glycol dialkyl ether, diethylene glycol dialkyl ether, triethylene glycol dialkyl ether, tetraethylene glycol dialkyl ether, polyethylene glycol dialkyl ether and other ethers; dimethylformamide, dimethyl acetoamide, N-methyl-2-pyrrolidone, dimethyl imidazolidinone, hexamethyl pholic triamide, dimethyl sulfoxide and other non-protonic polar solvents, methylene chloride, chloroform, dichloroethane, trichloroethane, trichloroethylene, other halogen type solvents, and freon type solvents.

The washing solvent can be a blend of two or more types. The washing solvent can contain components other than solvent, such as inorganic salts, surfactants, and cleaning agents.

Modification treatment as described above can be performed on the entire silicone hydrogel, or can be performed only on a portion of the silicone hydrogel such as only on the surface. If the modifications are performed only on the surface, the surface wettability alone can be enhanced without dramatically changing the physical properties of the entire silicone hydrogel.

If the water content of the silicone hydrogel of the present invention is too low, the silicone hydrogel will be hard, but if the water content is too high, water may evaporate from the surface of the silicone hydrogel and the wearer may experience a dry lens feeling during lens wear, so water content between about 20 and about 50 weight % are desirable, between about 25 and about 45 weight % is more preferable, and between about 30 and about 40 weight % is most preferable. Lower limit values are about 20 weight %, about 25 weight %, and about 30 weight %. Upper limit values are about 50 weight %, about 45 weight %, and about 40 weight %. Any of the preferred lower limit values and any of the preferred upper limit values can be combined together.

An elastic modulus of the silicone hydrogel of the present invention is preferably about 200 psi or less, in some embodiments about 100 psi or less, in order to obtain comfortable feel when being worn when the use is an ophthalmic lens and particularly a soft contact lens. The elastic modulus and elongation of the polymer of the present invention are measured by cutting out an array shape sample where a width of the narrowest section is 5 mm, and then stretching at a rate of 100 mm/minute using a tensile tester until it breaks. The initial gauge length of the sample (Lo) and sample length at break (Lf) are measured. Twelve specimens of each composition are measured and the average is reported. Tensile modulus is measured at the initial linear portion of the stress/strain curve. Percent elongation is =[(Lf−Lo)/Lo]×100. An elongation of the silicone hydrogel of the present invention is desirably about 100% or higher, in some embodiments about 150% or higher, and most in some embodiments about 200% or higher. Higher values mean that the silicone hydrogel will not easily break.

An advancing contact angle of the silicone hydrogel of the present invention is desirable about 70 degrees or less, about 60 degrees or less, and in some embodiments about 50 degrees or less, if the application is an ophthalmic lens.

As for the oxygen permeability of the silicone hydrogel of the present invention, the oxygen permeability constant is desirably about $50\times10^{-11}(cm^2/sec)mLO_2/(mL\cdot hPa)$ or higher, and in some embodiments $50\times10^{-11}(cm^2/sec)mLO_2/(mL\cdot hPa)$ or higher. The oxygen permeability constant of the polymer of the present invention is a value measured by a polarographic method.

As for the transparency of the silicone hydrogel of the present invention, the whole light transmissivity in the visible range is preferably about 85% or higher, more desirably about 90% or higher, and most preferably about 95% or higher when the application is an ophthalmic lens.

The silicone hydrogel of the present invention is suitable for use in medical implements such as ophthalmic lenses, endoscopes, catheters, transfusion tubes, gas transport tubes, stents, sheaths, cuffs, tube connectors, access ports, drainage bags, blood circuits, wound covering material, and various types of medicine carriers, but is particularly suitable for contact lenses, ophthalmic lenses, and artificial corneas.

The present invention will be described in further detail below through the use of working examples, but the present invention is not limited to these working examples.

MEASUREMENT METHOD FOR EXAMPLES
1-17

(1) Whole Light Transmissivity

The whole light transmissivity was measured using an SM color computer (model SM-7-CH, manufactured by Suga Test Instruments Co. Ltd.). Water on the lens sample is lightly wiped off, and then the sample is set in the light path and measured.

The thickness was measured using an ABC Digimatic Indicator (ID-C112, manufactured by Mitsutoyo Corporation), and samples with a thickness between 0.14 and 0.15 mm were measured.

(2) Elastic Modulus and Elongation

An array shaped sample with a width of 5 mm in the narrowest region was cut from the lens sample, the thickness was measured using an ABC Digimatic Indicator (ID-C112, manufactured by Mitsutoyo Corp., and then the elastic modulus and the elongation were measured using a Tensilon (RTM-100 manufactured by Toyo Baldwin Co. Ltd., cross head speed 100 mm/minute).

(3) Water Content

The weight of the silicone hydrogel when containing water (W1) and the weight when dry (W2) were measured and the water content was calculated from the following formula.

$$\text{Water content (\%)}=(W1-W2)/W1\times100$$

However, with the present invention, the condition where the silicone hydrogel contains water refers to a condition where the silicone hydrogel has been immersed in saline solution at 25° C. for 6 hours or longer. Furthermore, a dry condition for the silicone hydrogel refers to a condition where drying has been performed for 16 hours or longer in a vacuum dryer at 40° C.

(4) Dynamic Contact Angle

A short strip sample with a width of 5 mm was cut from the lens sample, and the dynamic contact angle was measured using a WET-6000 dynamic contact angle meter manufactured by Rhesca Corporation (immersion rate 7 mm/minute).

(5) Stress Zero Time

A 5 mm wide 1.5 cm long strip sample was cut from near the center of a lens, and measured using a CR-500DX rheometer manufactured by Sun Scientific Co. Ltd. The sample was mounted at a chuck width of 5 mm, and after stretching 5 mm at a rate of 100 mm/minute, this sample was returned to the original length (5 mm) at the same rate, and this cycle was repeated 3 times. From the moment that the stress became zero part way through returning the sample to the original length the second time, the length of time until the moment that stress began to be applied (stress was no longer zero) after beginning the third stretch cycle was determined to be the stress zero time. A shorter stress zero time indicates that the shape recovery properties of the silicone hydrogel are favorable, and a value of 2 seconds or less is preferable, 1.5 seconds or less is more preferable, and 1.2 seconds or less is most preferable.

Working Example 1

A silicone monomer expressed by the following formula (s1)

[FORMULA 13]

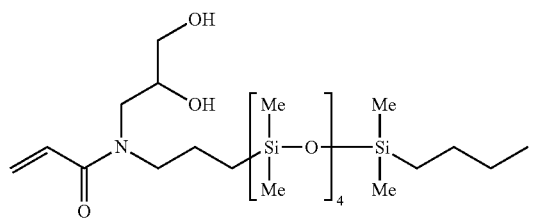

(0.925 g, 56.06 weight %), N,N-dimethyl acrylamide (0.510 g, 31.27 weight %), and non-silicone acrylamide monomer expressed by the following formula (h1)

[FORMULA 14]

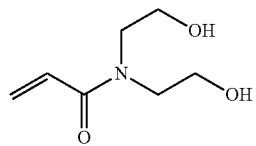

(0.017 g, 1 weight %), polyvinyl pyrrolidone (PVP K90, 0.132 g, 8 weight %), N,N'-methylene bisacrylamide (MBA, 0.018 g, 1.1 weight %), ultraviolet light absorber 2-(2'-hydroxy-5'-methacryloyloxy ethyl phenyl)-2H-benzotriazole (0.036 g, 2.22 weight %), 3-methyl-3-pentanol (3M3P, 1.350 g), and photoinitiator Irgacure 819 (0.004 g, 0.25 weight %) were blended together and mixed. The monomer blend obtained was degassed in an argon environment. The monomer blend was injected into the cavity in a transparent plastic (front curve side: Zeonor, base curve side: polypropylene) mold with a lens shape in a glove box under a nitrogen gas environment, and a lens was obtained by irradiating with light (Philips TL03, 1.6 mW/cm$^2$, 15 minutes) to harden. The lens obtained was peeled from the mold and impurities such as residual monomer were extracted by immersing for 70 minutes at room temperature in a 70% (volumetric ratio) aqueous solution of 2-propanol (IPA). After immersing in water for 10 minutes, the sample was placed submerged in a boric acid buffer solution (pH 7.1 to 7.3) in a 5 mL vial bottle, and the vial bottle was placed in an autoclave and boiled for 30 minutes at 120° C.

The whole light transmissivity, water content, elastic modulus, and elongation of the lens sample obtained were as shown in Table 1, and thus a lens was obtained which was transparent and had a balance between favorable physical properties.

TABLE 1

| | Silicone monomer | | Non-silicone acrylamide | | DMA | | water content | elastic modulus | Elong. | stress zero time | DCA |
|---|---|---|---|---|---|---|---|---|---|---|---|
| | monomer | wt % | Monomer | wt % | (wt %) | % T | (%) | (psi) | (%) | (sec) | (degree) |
| Working Example 1 | (s1) | 56.06 | (h1) | 1 | 31.27 | 92.0 | 40.7 | 95.2 | 254 | 0.81 | 36.5 |
| Working Example 2 | (s1) | 56.06 | (h1) | 2 | 30.27 | 92.0 | 37.0 | 86.0 | 293 | 0.97 | 43.8 |
| Working Example 3 | (s1) | 56.06 | (h1) | 3 | 29.27 | 91.7 | 38.0 | 107.9 | 306 | 0.99 | 45.2 |
| Working Example 4 | (s1) | 56.06 | (h1) | 5 | 27.27 | 91.6 | 36.1 | 95.4 | 364 | 0.93 | 47.5 |
| Working Example 5 | (s1) | 56.06 | (h1) | 7 | 25.27 | 91.5 | 37.3 | 116.9 | 370 | 0.85 | 50.1 |
| Working Example 6 | (s1) | 56.06 | (h1) | 12 | 20.27 | 91.8 | 34.7 | 135.5 | 295 | 0.91 | 50.2 |
| Working Example 7 | (s1) | 56.06 | (h2) | 1 | 31.27 | 91.2 | 40.0 | 103.0 | 232 | 1.01 | 35.2 |
| Working Example 8 | (s1) | 56.06 | (h2) | 2 | 30.27 | 91.1 | 37.7 | 97.9 | 276 | 1.01 | 35.9 |
| Working Example 9 | (s1) | 56.06 | (h2) | 3 | 29.27 | 91.6 | 37.6 | 96.2 | 282 | 0.95 | 28.5 |
| Working Example 10 | (s1) | 56.06 | (h2) | 5 | 27.27 | 91.1 | 37.0 | 113.5 | 309 | 0.97 | 33.9 |
| Working Example 11 | (s1) | 56.06 | (h2) | 7 | 25.27 | 91.6 | 36.3 | 143.3 | 292 | 1.09 | 34.5 |
| Comparative Example 1 | (s1) | 56.06 | HEAA | 1 | 31.27 | 82.0 | 41.0 | 85.5 | 369 | 1.05 | 30.2 |
| Comparative Example 2 | (s1) | 56.06 | HEAA | 2 | 30.27 | 43.8 | 42.0 | 81.4 | 306 | 0.93 | 33.9 |
| Comparative Example 3 | (s1) | 56.06 | HEAA | 3 | 29.27 | 18.7 | 43.6 | 88.7 | 324 | 0.93 | 36.6 |
| Comparative Example 4 | (s1) | 56.06 | HEAA | 5 | 27.27 | 17.7 | 42.2 | 87.0 | 302 | 0.91 | 27.8 |
| Comparative Example 5 | (s1) | 56.06 | HEAA | 7 | 25.27 | 11.8 | 41.1 | 89.1 | 292 | 0.81 | 32.4 |
| Comparative Example 6 | (s1) | 56.06 | HEAA | 12 | 20.27 | 8.6 | 41.1 | 102.5 | 186 | 0.85 | 38.6 |

Working Examples 2 Through 6

Lens samples were obtained by polymerizing in a manner similar to working example 1, except that the composition was changed as shown in Table 1. The appearance, whole light transmissivity, water content, elastic modulus, and elongation of the sample obtained were as shown in Table 1.

Working Example 7

A lens sample was fabricated in a manner similar to working example 1, except that the monomer expressed by the following formula (h2)

[FORMULA 15]

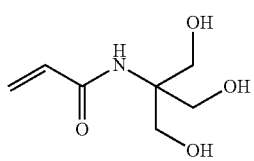

(h2)

was used in place of the monomer expressed by formula (h1) as the non-silicone acrylamide monomer. The appearance, whole light transmissivity, water content, elastic modulus, and elongation of the sample obtained were as shown in Table 1.

Working Examples 8 Through 11

A lens sample was obtained by polymerizing in a manner similar to working example 7, except that the composition was changed as shown in Table 1. The appearance, whole light transmissivity, water content, elastic modulus, and elongation of the sample obtained were as shown in Table 1.

Comparative Examples 1 Through 6

Lens samples were obtained by polymerizing in a manner similar to working example 1, except that 2-hydroxyethyl acrylamide (HEAA) as expressed in the following formula (h0)

[FORMULA 16]

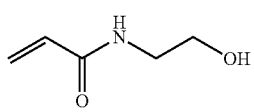

(h0)

was used in place of the monomer expressed by formula (h1) as the non-silicone acrylamide monomer, and the composition was as shown in Table 1. The appearance, whole light transmissivity, water content, elastic modulus, and elongation of the sample obtained were as shown in Table 1. From the data in Table 1 it can be seen that the whole lens transmissivity was undesirably low. Thus, non-silicone acrylamide monomers having a hydrogen on the nitrogen, and only one hydroxyl group do not provide the desired level of compatibility to the formulations. Comparative Examples 1-5 displayed desirable moduli.

Working Examples 12 Through 16

Lens samples were fabricated in a manner similar to working example 1 using the monomer expressed in the following formula (s2)

[FORMULA 17]

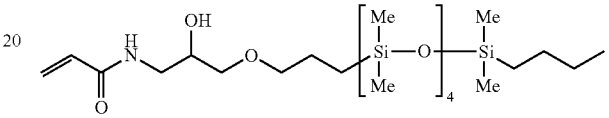

(s2)

as the silicone acrylamide monomer and the monomer expressed by formula (h1) or (h2) as the non-silicone acrylamide monomer at the composition shown in Table 2. The whole light transmissivity, water content, elastic modulus, and elongation of the sample obtained were as shown in Table 2.

TABLE 2

|  | Silicone monomer |  | Non-silicone acrylamide |  | DMA | trans- missivity | water content | elastic modulus | elon- gation | stress zero time | DCA |
| --- | --- | --- | --- | --- | --- | --- | --- | --- | --- | --- | --- |
|  | monomer | wt % | Monomer | wt % | (wt %) | (%) | (%) | (psi) | (%) | (sec) | (degree) |
| Working Example 12 | (s2) | 56.06 | (h1) | 5 | 27.27 | 88.9 | 40.9 | 94.0 | 272 | 0.94 | 47.4 |
| Working Example 13 | (s2) | 56.06 | (h1) | 7 | 25.27 | 88.9 | 40.1 | 87.2 | 220 | 1.00 | 53.5 |
| Working Example 14 | (s2) | 56.06 | (h1) | 12 | 20.27 | 89.4 | 39.5 | 83.1 | 232 | 0.87 | 47.5 |
| Working Example 15 | (s2) | 56.06 | (h1) | 20 | 12.27 | 87.1 | 40.3 | 79.8 | 217 | 0.83 | 55.4 |
| Working Example 16 | (s2) | 56.06 | (h2) | 7 | 25.27 | 87.3 | 39.9 | 89.0 | 297 | 0.88 | 44.8 |
| Comparative Example 7 | (s2) | 56.06 | HEAA | 5 | 27.27 | 3.2 | 44.1 | 68.5 | 253 | 1.15 | 53.5 |
| Comparative Example 8 | (s2) | 56.06 | HEAA | 7 | 25.27 | 3.3 | 44.0 | 68.1 | 213 | 1.02 | 54.4 |
| Comparative Example 9 | (s2) | 56.06 | HEAA | 12 | 20.27 | 3.9 | 43.6 | 65.3 | 256 | 1.01 | 61.7 |

Comparative Examples 7 Through 9

Lens samples were fabricated in a manner similar to working example 1 using the monomer expressed by formula (s2) as the non-silicone acrylamide monomer and using HEAA expressed by formula (h0) as the silicone acrylamide monomer, at the composition shown in Table 2. The whole light transmissivity, water content, elastic modulus, and elongation of the sample obtained were as shown in Table 2. Comparing the results of Comparative Examples 6-9 with Examples 12-16 it can be seen that HEAA is not sufficient as a compatibilizer for these systems. This is surprising as the methacrylate version, 2-hydroxyethyl methacrylate does function as a compatibilizing component in silicone hydrogels. However, the formulations of Comparative Examples 6-9 which use HEAA display desirable, low moduli.

Working Example 17

The components shown in Table 3 were blended together with N,N'-methylene bisacrylamide (MBA, 1.1 weight %), 2-(2'-hydroxy-5'-methacryloyloxy ethyl phenyl)-2H-benzotriazole (Norbloc, 2.2 weight %), photoinitiator Irgacure 819 (0.25 weight %) and tertiary amyl alcohol (t-AA) as the solvent in a ratio of 45 wt % diluents to 55 wt % components, and mixed. The following acronyms are used in Table 3.

(s1) is a silicone monomer of the formula:

[FORMULA 18]

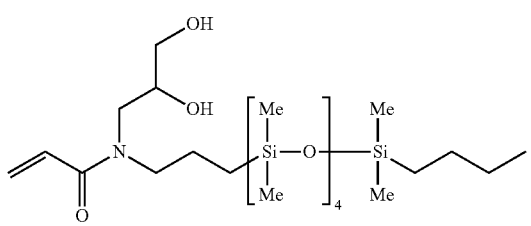

(s1)

(h1) is a non-silicone acrylamide monomer (NSA in Table 3) expressed by the following formula:

[FORMULA 19]

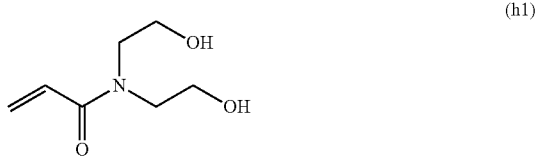

(h1)

DMA N,N-dimethyl acrylamide
PVP polyvinyl pyrrolidone (PVP K90),

The monomer blend obtained was degassed under vacuum. The monomer blend was injected into the cavity in a transparent plastic (front curve side: Zeonor, base curve side: polypropylene) mold with a lens shape in a glove box under a nitrogen gas environment, and a lens was obtained by irradiating with light (Philips TL03, 1.5 mW/cm$^2$, 15 minutes) to cure. The lens were released from the mold and impurities such as residual monomer were removed by immersing in 70/30 (vol/vol) mixture of isopropol alcohol (IPA) and DI water for ~90 minutes at room temperature. After extraction, the lenses were then immersed in DI water for ~90 minutes to remove the IPA and then stored in standard packing solution to equilibrate. Individual lenses were placed in glass vials with ~5 ml of packing solution and autoclaved at ~120° C. for 30 minutes. The measured value for lens haze, water content, dynamic contact angle (DCA) and elastic modulus are listed in Table 3. Thus, a lens was obtained which was sufficiently transparent and exhibited a balance of favorable physical properties.

The advancing contact angle in Examples 17-19 and Examples 31-36 was measured as follows. Four samples from each set were prepared by cutting out a center strip from the lens approximately 5 mm in width and equilibrated in packing solution. The wetting force between the lens surface and borate buffered saline is measured at 23° C. using a Wilhelmy microbalance while the sample is being immersed into or pulled out of the saline. The following equation is used $$F = 2\gamma p \cos\theta \text{ or } \theta = \cos^{-1}(F/2\gamma p)$$

where F is the wetting force, γ is the surface tension of the probe liquid, p is the perimeter of the sample at the meniscus and θ is the contact angle. The advancing contact angle is obtained from the portion of the wetting experiment where the sample is being immersed into the packing solution. Each sample was cycled four times and the results were averaged to obtain the advancing contact angles for the lens.

Haze in Examples 17-19 and Examples 31-36 was measured by placing a hydrated test lens in borate buffered saline in a clear 20×40×10 mm glass cell at ambient temperature above a flat black background, illuminating from below with a fiber optic lamp (Titna Tool Supply Co. fiber optic light with 0.5" diameter light guide set at a power setting of 4-5.4) at an angle 66° normal to the lens cell, and capturing an image of the lens from above, normal to the lens cell with a video camera (DVC 1300C:19130 RGB camera with Navitar TV Zoom 7000 zoom lens) placed 14 mm above the lens platform. The background scatter is subtracted from the scatter of the lens by subtracting an image of a blank cell using EPIX XCAP V 1.0 software. The subtracted scattered light image is quantitatively analyzed, by integrating over the central 10 mm of the lens, and then comparing to a −1.00 diopter CSI Thin Lens®, which is arbitrarily set at a haze value of 100, with no lens set as a haze value of 0. Five lenses are analyzed and the results are averaged to generate a haze value as a percentage of the standard CSI lens.

Modulus in Examples 17-19 and Examples 31-36 was measured by using the crosshead of a constant rate of movement type tensile testing machine equipped with a load cell that is lowered to the initial gauge height. A suitable testing machine includes an Instron model 1122. A dog-bone shaped sample having a 0.522 inch length, 0.276 inch "ear" width and 0.213 inch "neck" width is loaded into the grips and elongated at a constant rate of strain of 2 in/min. until it breaks. The initial gauge length of the sample (Lo) and sample length at break (Lf) are measured. Twelve specimens of each composition are measured and the average is reported. Tensile modulus is measured at the initial linear portion of the stress/strain curve. Percent elongation is $=[(Lf-Lo)/Lo]\times 100$.

Working Examples 18 and 19

A lens sample was obtained by polymerizing in a manner similar to working example 17, except that the composition was changed as shown in Table 3. The measured value for lens haze, water content, dynamic contact angle (DCA) and elastic modulus are listed in Table 3.

Working Examples 20 Through 24

Lens samples were fabricated in a manner similar to working example 17 except that the composition was changed as shown in Table 3. The measured value for lens haze, water content, dynamic contact angle (DCA) and elastic modulus are listed in Table 3. Comparing Examples 20-22 to Example 17, it can be seen that when the PVP content is reduced, the resulting lenses are clear, but less wettable. Comparing Examples 23-25 to Example 17, it can be seen that when the PVP content is increased or when a non-silicone monomer is changed into (h2), the resulting lenses are wettable, but less clear.

Working Example 25

A lens sample was fabricated in a manner similar to working example 17, except that the non-silicone (meth)acrylamide monomer of formula (h2) was used.

[FORMULA 20]

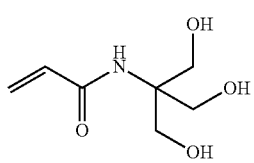

(h2)

The measured value for lens haze, water content, dynamic contact angle (DCA) and elastic modulus are listed in Table 3.

TABLE 3

| Ex# | [s1] wt % | [NSA] Wt % | [DMA] wt % | [PVP] wt % | Haze % CSI | % H₂O | Elastic modulus psi | DCA |
|---|---|---|---|---|---|---|---|---|
| 17 | 56 | 3 | 30 | 8 | 21 ± 2 | 45 | 120 ± 10 | 51 ± 5 |
| 18 | 45 | 3.4 | 40 | 8 | 18 ± 1 | 53 | 113 ± 9 | 48 ± 16 |
| 19 | 48 | 3.4 | 39 | 7 | 33 ± 1 | 51 | 120 ± 10 | 54 ± 13 |
| 20 | 55 | 3 | 36 | 2 | 17 ± 1 | 39 | 164 ± 16 | lw* |
| 21 | 40 | 3 | 51 | 2 | 16 ± 1 | 55 | 130 ± 7 | lw* |
| 22 | 51 | 3 | 38 | 5 | 23 ± 1 | 44 | 122 ± 11 | lw* |
| 23 | 55 | 3 | 26 | 12 | 75 ± 1 | 48 | 132 ± 6 | 75 ± 14 |
| 24 | 45 | 3 | 40 | 10 | 42 ± 2 | 55 | 103 ± 7 | 50 ± 8 |
| 25 | 56 | 3 | 30 | 8 | 83 ± 33 | 45 | 117 ± 7 | 57 ± 4 | lw = less-wetting using an evaporator. The crude material was purified by silica gel column chromatography (tetrahydrofuran as eluent). The monomer expressed by the following formula (h3)

[FORMULA 21]

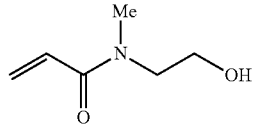

(h3)

was obtained.

Monomer Synthesis 2

A monomer was synthesized in a manner similar to Monomer synthesis 1, except that 1-(N-methylamino)-2,3-dihydroxypropane was used in place of 2-(N-methylamino)ethanol. The monomer expressed by the following formula (h4)

[FORMULA 22]

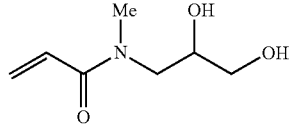

(h4)

was obtained.

Working Example 26 Through 27

A lens sample was fabricated in a manner similar to working example 1, except that the monomer expressed by the formula (h3) and (h4) was used in place of the monomer expressed by formula (h1) as the non-silicone acrylamide monomer, and except that the composition was changed as shown in Table 4. The appearance, whole light transmissivity, water content, elastic modulus, and elongation of the sample obtained were as shown in Table 4.

TABLE 4

| | silicone acrylamide | | non-silicone acrylamide | | N,N-dimethylacrylamide | transmissivity | water content | elastic modulus | elongation | stress zero time | Advancing contact angle |
|---|---|---|---|---|---|---|---|---|---|---|---|
| | formula | (wt %) | formula | (wt %) | (wt %) | (%) | (%) | (psi) | (%) | (sec) | (degree) |
| Working Example 26 | (s1) | 56.06 | (h3) | 7 | 25.27 | 90.3 | NA | NA | NA | NA | NA |
| Working Example 27 | (s1) | 56.06 | (h4) | 7 | 25.27 | 91.9 | 37.4 | 151 | 151 | 0.80 | 58.5 |

NA = not analyzed

Monomer Synthesis 1

2-(N-methylamino)ethanol (7.88 g, 0.105 mol) and tetrahydrofuran (100 mL) were placed in a 300 mL 3-necked flask, acrylic acid chloride (4.1 mL, 0.05 mol) was added by drops using a dropping funnel over a period of approximately 20 minutes while in an ice bath (−10 to −5° C.).

2 hours after the start of dropwise addition, the reaction solution was filtered and the precipitate was washed with hexane that had been cooled in a refrigerator. The wash solution was combined with the filtrate, and then concentrated Thus, the present invention relates to a silicone hydrogel, and this silicone hydrogel is suitable for use in medical devices, and particularly suitable for use in contact lenses, intraocular lenses, artificial cornea, and the like.

The invention claimed is:

1. A silicone hydrogel obtained by polymerizing a polymerization mix containing a plurality of monomers containing (a) about 30 to about 98 weight % of at least one silicone monomer represented by the general formulae (b1), (b2):

[FORMULA 3]

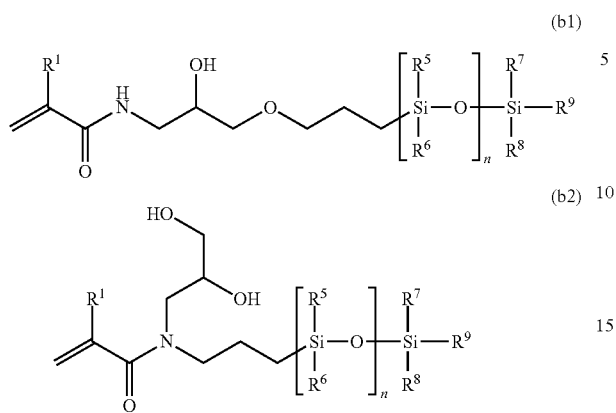

wherein in the chemical formulae (b1) or (b2), $R^1$ independently represents a hydrogen atom or a methyl group; $R^5$ to $R^9$ independently represent alkyl groups with between 1 and 20 carbon atoms or aryl groups with between 6 and 20 carbon atoms; and n is a natural number in the range from 1 to 50); and (b) about 1 to about 50 weight % of at least one non-silicone (meth)acrylamide monomer represented by

[FORMULA 1]

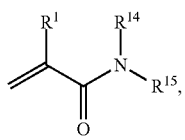

wherein $R^1$ is hydrogen or methyl;
at least one of $R^{14}$ and $R^{15}$ is a C1-20 alkyl group substituted with at least one hydroxyl group, and
with the proviso that when;
i) one of $R^{14}$ and $R^{15}$ is hydrogen
ii) the other of $R^{14}$ and $R^{15}$ is substituted with at least two hydroxyl groups,
wherein said weight percent based upon total amount of monomer components and polymer components in the monomer mix and wherein the silicone (meth)acrylamide monomer and non-silicone (meth)acrylamide monomer are present in the monomer mix in an amount of about 90% or more by weight with respect to a total amount of the monomers in the monomer mix.

2. The silicone hydrogel according to claim 1, wherein said non-silicone (meth)acrylamide monomer comprises two or more hydroxyl groups.

3. The silicone hydrogel according to claim 1, wherein said non-silicone (meth)acrylamide monomer comprises one hydroxyl group and no amide hydrogen.

4. The silicone hydrogel according to any of claim 1 to claim 3, wherein the polymerization mix further comprises about 1 to about 30 weight % of at least one hydrophilic polymer with a molecular weight of about 1000 or more; wherein said weight percent is based upon total amount of monomer components and polymer components in the monomer mix.

5. The silicone hydrogel according to any one of claim 1 to claim 3, wherein the silicone monomers have at least one hydroxyl group.

6. The silicone hydrogel according to claim 1, wherein the silicone (meth)acrylamide monomer is represented by the following general formula (a1) or (a2):

[FORMULA 2]

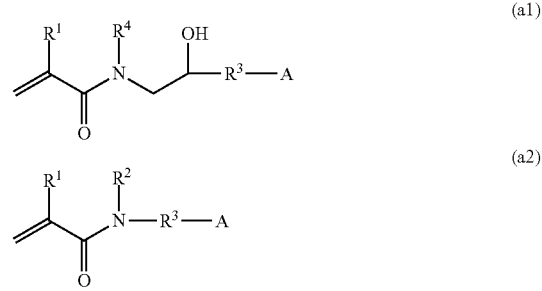

wherein in the chemical formulae (a1) and (a2), $R^1$ independently represents a hydrogen atom or a methyl group; $R^2$ represents an alkyl group having between 1 and 20 carbon atoms and having at least one hydroxyl group; $R^3$ independently represents an alkylene group with between 1 and 20 carbon atoms or an arylene group having between 6 and 20 carbon atoms, which may have substitution groups; $R^4$ represents H, an aryl group or alkyl group with between 1 and 20 carbon atoms which may have substitution groups; and A represents a siloxanyl group.

7. The silicone hydrogel according to claim 1, wherein the silicone (meth)acrylamide monomer further comprises at least one additional silicone (meth)acrylamide represented by the general formulae (b3) or (b4):

[FORMULA 4]

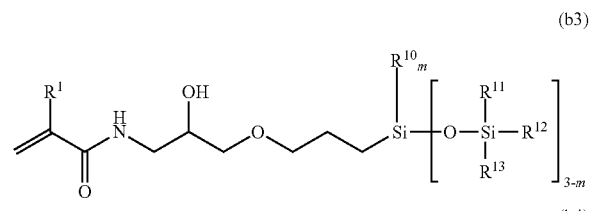

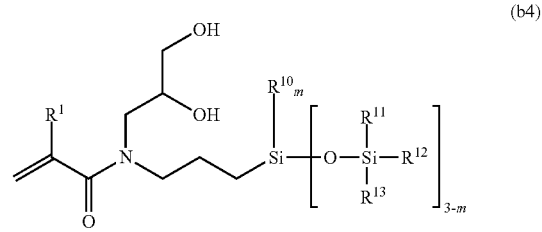

wherein in the chemical formulae (b3) or (b4), $R^1$ independently represents a hydrogen atom or a methyl group; $R^{10}$ to $R^{13}$ independently represent alkyl groups with between 1 and 20 carbon atoms or aryl groups with between 6 and 20 carbon atoms; and m is a natural number in the range from 0 to 2.

8. The silicone hydrogel according to any one of claims 1-3, 5 or 6, wherein the non-silicone (meth)acrylamide monomer is represented by any one of the following general formulae (c1) to (c3):

[FORMULA 5]

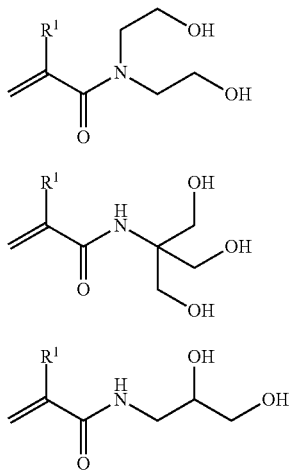

wherein in the chemical formulae (c1) to (c3), $R^1$ independently represents a hydrogen atom or a methyl group.

9. The silicone hydrogel according to claim 4, wherein, the at least one hydrophilic polymer is selected from a group consisting of poly-N-vinyl pyrrolidone, poly-N-vinyl-2-piperidone, poly-N-vinyl-2-caprolactam, poly-N-vinyl-3-methyl-2-caprolactam, poly-N-vinyl-3-methyl-2-piperidone, poly-N-vinyl-4-methyl-2-piperidone, poly-N-vinyl-4-methyl-2-caprolactam, poly-N-vinyl-3-ethyl-2-pyrrolidone, poly-N-vinyl-4,5-dimethyl-2-pyrrolidone, polyvinyl imidazole, poly-N-vinyl formamide, poly-N-vinyl(methyl)acetamide, poly-N-methyl-N-vinyl(methyl)acetamide, poly-N-vinyl-N-methylpropionamide, poly-N-vinyl-N-methyl-2-methylpropionamide, poly-N-vinyl-2-methylpropionamide, poly-N-vinyl-N,N'-dimethylurea, poly-N,N-dimethyl acrylamide, poly-N,N-diethyl acrylamide, poly-N-isopropyl acrylamide, polyvinyl alcohol, polyacrylate, polyethylene oxide, poly-2-ethyl oxazoline, heparine, polysaccharide, poly-acryloyl morpholine, and mixtures and copolymers thereof.

10. The silicone hydrogel according to claim 4, wherein the at least one hydrophilic polymer is selected from a group consisting of polyvinyl pyrrolidone, poly(N,N-dimethyl acrylamide), poly-N-vinyl(methyl)acetamide, polyacrylate, polyvinyl alcohol, and copolymers thereof.

11. The silicone hydrogel according to claim 1, wherein the composition amount of the (meth)acrylamide monomer with respect to the total amount of monomer components in the monomer mix is 95% or more by weight.

12. The silicone hydrogel according to any one of claim 1-3, 5, 6, or 7-9, wherein, the monomer mix further comprises about 1 to about 50 weight % at least one non-silicone (meth)acrylamide monomer having no hydroxyl group.

13. The silicone hydrogel according to claim 10, wherein, the non-silicone (meth)acrylamide monomer having no hydroxyl group is selected from a group consisting of (meth)acrylamide, N,N-dimethyl(meth)acrylamide, N,N-diethyl(meth)acrylamide, N-isopropyl(meth)acrylamide, (meth)acryloyl morpholine, and N-methoxy methyl(meth)acrylamide.

14. A medical device made from the silicone hydrogel described in any one of claim 1-3, 5, 6, 7-9, or 11.

15. The medical device according to claim 12, wherein the medical device is contact lenses, artificial corneas, endoscopes, catheters, transfusion tubes, gas transport tubes, stents, sheaths, cuffs, tube connectors, access ports, drainage bags, blood circuits, wound covering material, and medicine carriers.

16. An ophthalmic lens made from a silicone hydrogel described in any one of claim 1-3, 5, 6, 7-9, or 13.

17. A contact lens made from a silicone hydrogel described in any one of claim 1-3, 5, 6, 7-9, 11, or 13.

18. The silicone hydrogel of claim 1 wherein $R^{14}$ are $R^{15}$ are independently is selected from the group consisting of C1-10 alkyl groups substituted with at least one hydroxyl group.

19. The silicone hydrogel of claim 1 wherein $R^{14}$ are $R^{15}$ are independently selected from the group consisting of C1-6 alkyl groups substituted with at least one hydroxyl group.

* * * * *

UNITED STATES PATENT AND TRADEMARK OFFICE
CERTIFICATE OF CORRECTION

PATENT NO.        : 8,476,389 B2                                Page 1 of 1
APPLICATION NO.   : 13/048252
DATED             : July 2, 2013
INVENTOR(S)       : Maggio et al.

It is certified that error appears in the above-identified patent and that said Letters Patent is hereby corrected as shown below:

In the Claims

Column 26, line 65, Claim 8:   claims 1-3, 5 or 6 should read --claims 1-3, 6, or 7--

Column 28, line 11, Claim 12:  1-3, 5, 6, or 7-9, should read --1-3, 6, 7 or 9-11,--

Column 28, line 14, Claim 13:  The silicone hydrogel according to claim 10, should read --The silicone hydrogel according to claim 12--

Column 28, line 23, Claim 14:  described in any one of claim 1-3, 5, 6, 7-9, or 11. should read --described in any one of claims 1-3, 6, 7, 9-11 or 13.--

Column 28, line 24, Claim 15: The medical device according to claim 12, should read --The medical device according to claim 14,--

Column 28, line 30, Claim 16:  described in any one of claim 1-3, 5, 6, 7-9, or 13. should read --described in any one of claims 1-3, 6, 7, 9-11, 13 or 15.--

Column 28, line 34, Claim 18:  are independently is selected should read --are independently selected--

Signed and Sealed this
Eighth Day of April, 2014

Michelle K. Lee
*Deputy Director of the United States Patent and Trademark Office*